US011058341B2

(12) United States Patent
Hori

(10) Patent No.: US 11,058,341 B2
(45) Date of Patent: Jul. 13, 2021

(54) RECONSTRUCTING DEVICE, RECONSTRUCTING METHOD, PROGRAM, AND INFORMATION RECORDING MEDIUM

(71) Applicant: RIKEN, Saitama (JP)

(72) Inventor: Gen Hori, Saitama (JP)

(73) Assignee: RIKEN, Saitama (JP)

(*) Notice: Subject to any disclaimer, the term of this patent is extended or adjusted under 35 U.S.C. 154(b) by 698 days.

(21) Appl. No.: 15/576,639

(22) PCT Filed: Jun. 2, 2016

(86) PCT No.: PCT/JP2016/066445
§ 371 (c)(1),
(2) Date: Feb. 21, 2018

(87) PCT Pub. No.: WO2016/195029
PCT Pub. Date: Dec. 8, 2016

(65) Prior Publication Data
US 2019/0053727 A1 Feb. 21, 2019

(30) Foreign Application Priority Data

Jun. 2, 2015 (JP) .............................. JP2015-112113

(51) Int. Cl.
*A61B 5/316* (2021.01)
*A61B 5/00* (2006.01)
(Continued)

(52) U.S. Cl.
CPC ............. *A61B 5/316* (2021.01); *A61B 5/291* (2021.01); *A61B 5/4064* (2013.01);
(Continued)

(58) Field of Classification Search
CPC . A61B 5/04012; A61B 5/7253; A61B 5/7203; A61B 5/4064; A61B 5/7246;
(Continued)

(56) References Cited

U.S. PATENT DOCUMENTS

| 5,263,488 | A | * | 11/1993 | Van Veen | .............. | G06K 9/0057 600/544 |
| 2013/0226613 | A1 | * | 8/2013 | Srinivasan | .............. | G06F 19/00 705/3 |
| 2019/0304090 | A1 | * | 10/2019 | Wang | ................... | G06K 9/6247 |

FOREIGN PATENT DOCUMENTS

| CN | 106291470 A | * | 1/2017 |
| JP | 2010-234000 | | 10/2010 |

(Continued)

OTHER PUBLICATIONS

Zavodsky et al., Evaluation of an Innovation Variance Methodology for Real-Time Data Reduction of Satellite Data Streams, ams.confex. com (Year: 2006).*

(Continued)

*Primary Examiner* — Jacqueline Cheng
*Assistant Examiner* — Tho Q Tran
(74) *Attorney, Agent, or Firm* — Ohlandt, Greeley, Ruggiero & Perle, L.L.P.

(57) ABSTRACT

Measured values are obtained from multiple points of a target by thinning out and measuring or measuring and then thinning out. A calculator 102 of a reconstructing device 101 calculates a variance/covariance matrix of the multiple points from calibration values measured at different points at the same time among the measured values. A corrector 103 obtains corrected values by interpolating unmeasured values for times when the measured values are absent at each of the multiple points. Here, the corrector 103 obtains the corrected values so that a variance/covariance matrix of the multiple points that should be calculated from the corrected values matches or approximates to the variance/covariance matrix calculated from the calibration values.

13 Claims, 11 Drawing Sheets

(51) Int. Cl.
*G16H 50/70* (2018.01)
*A61B 5/291* (2021.01)
*G16H 50/20* (2018.01)
*A61B 5/369* (2021.01)
*G16H 40/40* (2018.01)

(52) U.S. Cl.
CPC .......... *A61B 5/7203* (2013.01); *A61B 5/7246* (2013.01); *A61B 5/7253* (2013.01); *G16H 40/40* (2018.01); *G16H 50/20* (2018.01); *G16H 50/70* (2018.01); *A61B 5/369* (2021.01)

(58) Field of Classification Search
CPC .... A61B 5/0478; A61B 5/0476; G16H 40/40; G16H 50/70; G16H 50/20; F02D 41/249; G06F 15/82; G06F 17/16; G06F 17/18
USPC ........................................................ 600/544
See application file for complete search history.

(56) References Cited

FOREIGN PATENT DOCUMENTS

| | | |
|---|---|---|
| JP | 2014-230717 | 12/2014 |
| JP | 2015-80582 | 4/2015 |

OTHER PUBLICATIONS

Majumdar et al., A Low-Rank Matrix Recovery Approach for Energy Efficient EEG Acquisition for a Wireless Body Area Network, Sensors 2014, vol. 14, pp. 15729-15748, ISSN 1424-8220, Aug. 25, 2014.

International Search Report dated Aug. 23, 2016 from corresponding International PCT Application No. PCT/JP2016/066445.

* cited by examiner

FIG. 3

| | | | | | | | | | | | | | | | | | |
|---|---|---|---|---|---|---|---|---|---|---|---|---|---|---|---|---|---|
| AF3 | | | | | | | | | | | | | | | | | |
| F7 | | | | | | | | | | | | | | | | | |
| F3 | | | | | | | | | | | | | | | | | |
| FC5 | | | | | | | | | | | | | | | | | |
| T7 | | | | | | | | | | | | | | | | | |
| P7 | | | | | | | | | | | | | | | | | |
| O1 | | | | | | | | | | | | | | | | | |
| O2 | | | | | | | | | | | | | | | | | |
| P8 | | | | | | | | | | | | | | | | | |
| T8 | | | | | | | | | | | | | | | | | |
| FC6 | | | | | | | | | | | | | | | | | |
| F4 | | | | | | | | | | | | | | | | | |
| F8 | | | | | | | | | | | | | | | | | |
| AF4 | | | | | | | | | | | | | | | | | |

RECONSTRUCTING DEVICE, RECONSTRUCTING METHOD, PROGRAM, AND INFORMATION RECORDING MEDIUM

TECHNICAL FIELD

The present disclosure relates to a reconstructing device reconstructing activity at multiple points at times from measured values obtained from multiple points of a target by thinning out and measuring or measuring and then thinning out, a reconstructing method, a program for realizing them by a computer, and a non-transitory computer-readable information recording medium storing the program.

BACKGROUND ART

In the prior art, techniques of measuring a target at multiple points and then thinning out measured values to compress the data volume are proposed. For example, Non Patent Literature 1 reported that original brain electrical activity was successfully reconstructed from approximately 40% remaining data after thinning out measured values obtained by measuring the brain waves at multiple points on the head of a person.

On the other hand, with an electroencephalograph using multiple scalp electrodes, an analog/digital converter is connected to each electrode and output digital information can be processed by a computer. As just stated, techniques of measuring electrical activity at multiple points of a target are widely used.

CITATION LIST

Non Patent Literature

Non Patent Literature 1: Angshul Majumdar, Anupriya Gogna and Rabab Ward, A Low-Rank Matrix Recovery Approach for Energy Efficient EEG Acquisition for a Wireless Body Area Network, Sensors 2014, Vol. 14, pp. 15729-15748, ISSN 1424-8220, Aug. 25, 2014.

SUMMARY OF INVENTION

Technical Problem

However, preparing many analog/digital converters leads to a problem that the manufacturing cost and/or the size of a measuring device is increased. On the other hand, the technique disclosed in the Non Patent Literature 1 can reduce the data volume only to approximately 40%.

Therefore, there is a demand for a technique of reconstructing original electrical activity from digital information acquired by converting electrical activity obtained by a measuring device measuring a target at multiple points with one or a smaller number of analog/digital converters than the number of multiple points. More generally, there is a demand for a technique of reconstructing original activity from thinned-out measurements at multiple points of a target.

The present disclosure is intended to solve the above problem and an objective of the disclosure is to provide a reconstructing device reconstructing activity at multiple points at times from measured values obtained from multiple points of a target by thinning out and measuring or measuring and then thinning out, a reconstructing method, a program for realizing them by a computer, and a non-transitory computer-readable information recording medium storing the program.

Solution to Problem

In the present disclosure, the reconstructing device processes measured values obtained from multiple points of a target by thinning out and measuring or measuring and then thinning out, also called under-sampling.

The reconstructing device calculates a variance/covariance matrix of the multiple points from calibration values measured at different points at the same time among the measured values, and obtains corrected values by interpolating unmeasured values for times when the measured values are absent at each of the multiple points.

Here, the reconstructing device obtains the corrected values so that a variance/covariance matrix of the multiple points that should be calculated from the corrected values approximates to the variance/covariance matrix calculated from the calibration values.

In another aspect of the present disclosure, a measuring device successively analog/digital-converts by means of a single analog/digital converter and outputs (a) electrical activity measured at multiple points of a target at the same time in a calibration mode, and (b) electrical activity measured at the multiple points at different times in a measuring mode.

On the other hand, the reconstructing device calculates a variance/covariance matrix of the multiple points from calibration values output by the measuring device in the calibration mode, and obtains corrected values from measured values output by the measuring device in the measuring mode by interpolating unmeasured values for times when the measured values are not output at each of the multiple points.

Then, the reconstructing device obtains the corrected values so that a variance/covariance matrix of the multiple points that should be calculated from the corrected values approximates to the variance/covariance matrix calculated from the calibration values.

Advantageous Effects of Invention

The present disclosure can provide a reconstructing device reconstructing activity at multiple points at times from measured values obtained from multiple points of a target by thinning out and measuring or measuring and then thinning out, a reconstructing method, a program for realizing them by a computer, and a non-transitory computer-readable information recording medium storing the program.

BRIEF DESCRIPTION OF DRAWINGS

FIG. 3 is a time table presenting the points and the times of electrical activity obtained in the calibration mode;

DESCRIPTION OF EMBODIMENTS

An embodiment of the present disclosure will be described below. Here, this embodiment is given for the purpose of explanation and does not confine the scope of the present disclosure. Therefore, a person in the field can adopt an embodiment in which some or all elements of this embodiment are replaced with those equivalent thereto. Moreover, the elements described in each practical example can be omitted as appropriate depending on the intended use. As just stated, any embodiment configured according to the principle of the present disclosure is included in the scope of the present disclosure.

For easier understanding, in the following explanation, first, an embodiment in which the measuring target is a single person and the electrical activity is the potentials measured at points using multiple electrodes will be described. Then, embodiments to apply to other fields will be described.

(Configuration of an Electroencephalograph)

Figure 1:
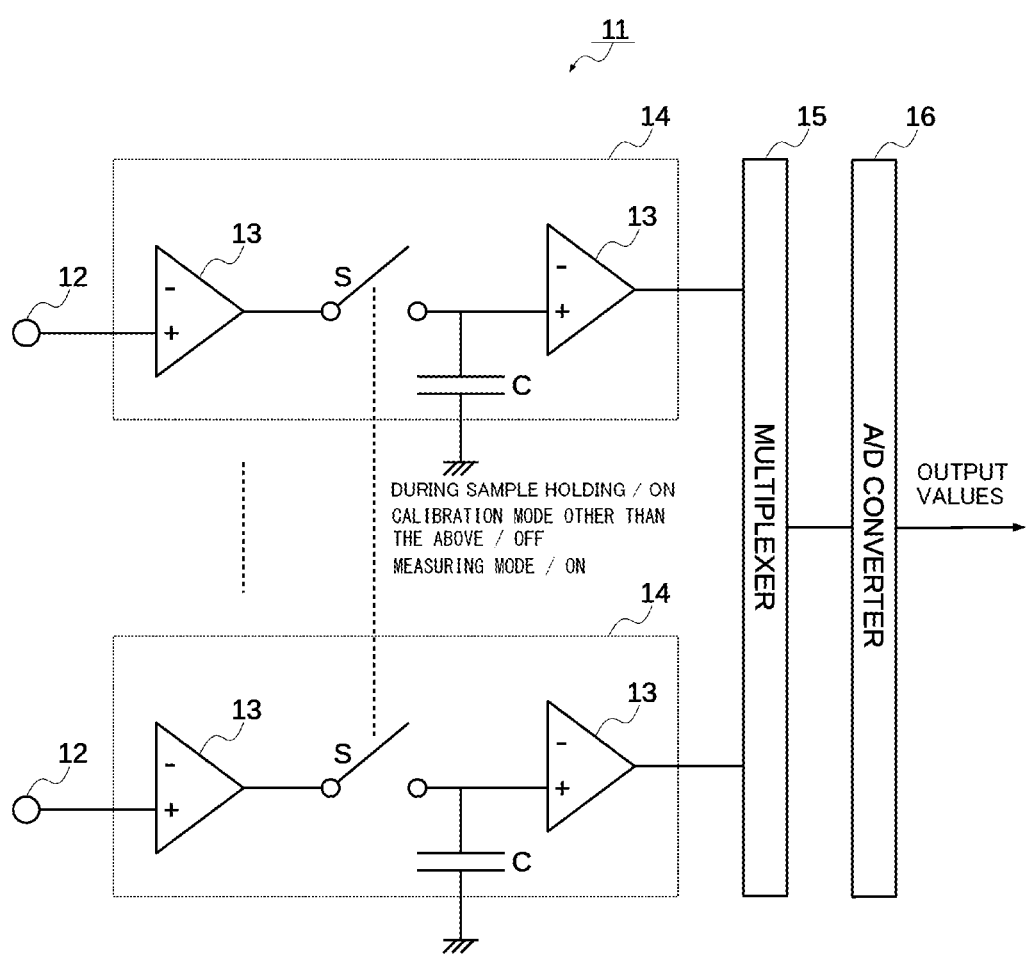
FIG. 1 is an explanatory diagram showing the configuration of an electroencephalograph according to a practical example of the present disclosure.

An inexpensive electroencephalograph capable of measuring digital information processed in this embodiment will be described below. As the electroencephalograph according to this embodiment, an electroencephalograph having the appearance of a cap with scalp electrodes making contact with multiple points of the scalp of a subject is used to measure the scalp potential. FIG. 1 is an explanatory diagram showing the configuration of an electroencephalograph according to a practical example of the present disclosure. The following explanation will be made with reference to this figure.

As shown in the figure, on an electroencephalograph 11 according to this embodiment, multiple electrodes 12 making contact with the scalp of a person are prepared and the measured potentials are amplified by amplifiers 13.

Then, in the calibration mode, signals amplified by the amplifiers 13 are held by sample holding circuits 14 for a specific time and given to a multiplexer 15. In the measuring mode, signals amplified by the amplifiers 13 are directly given to the multiplexer 15 as they are.

The multiplexer selectively gives any one of the given signals to an analog/digital (A/D) converter 16 at each clock. In the electroencephalograph 11 according to this embodiment, the clock number F=2048 Hz. However, the clock number may be changed as appropriate depending on the measuring environment and/or the intended use.

In the electroencephalograph 11 according to this embodiment, signals obtained from multiple electrodes are selected by the multiplexer 15 and successively output. In other words, the potentials measured at the electrodes are thinned out and then A/D-converted by the A/D converter 16.

Figure 2:
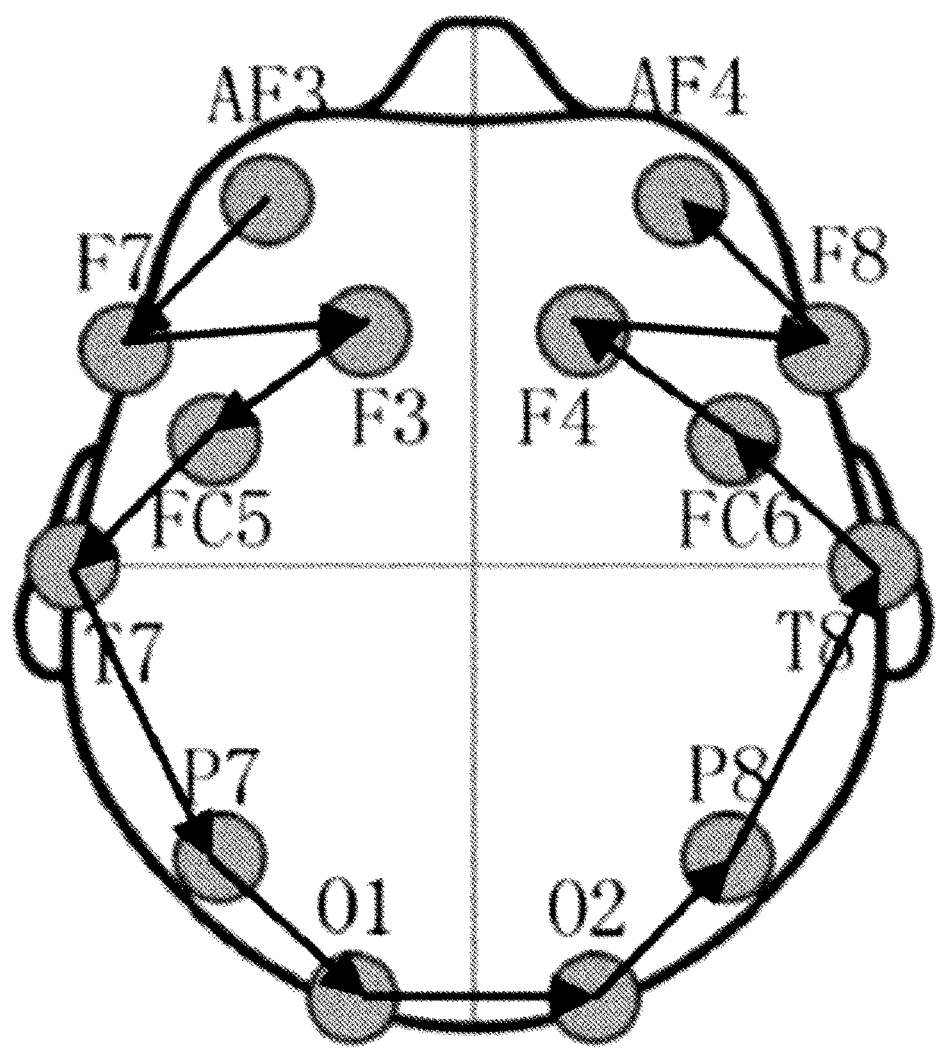
FIG. 2 is an explanatory diagram showing exemplary placement of the scalp electrodes.

FIG. 2 is an explanatory diagram showing exemplary placement of the scalp electrodes. The following explanation will be made with reference to this figure. In the example shown in this figure, the number of scalp electrodes, N, is 14 (AF3, F7, F3, FC5, T7, P7, O1, O2, P8, T8, FC6, F4, F8, AF4). Therefore, when a potential measured at an electrode is A/D-converted by the A/D converter 16 at a clock, the above setting requires a time length N/F=14/2048 seconds=6.836 ms for making a round of all electrodes. In order to provide a proper respite between a round and the next round, dummy electrodes may be assumed. For example, when two dummy electrodes are provided, N=14+2 and the round cycle is N/F=16/2048 seconds=7.8135 ms.

In the calibration mode, all sample holding circuits 14 are synchronized. Then, the sample holding circuits 14 each acquire the potential of the electrode 12 connected thereto in each round cycle and hold the potential until the next acquisition. In other words, switches S of all sample holding circuits 14 are connected for a moment (a very short length of time for charging capacitors C) in a round cycle and the switches S are opened (disconnected) at other times.

On the other hand, in the measuring mode, the switches S of all sample holding circuits 14 are kept connected.

The number of measuring points, N, and the frequency of A/D conversion, F, can be changed as appropriate. Moreover, as the measuring points, the brain surface may invasively be measured. Moreover, as the electrical activity to measure, other than the potential, the electrode contact resistance may be measured, or the magnetic field occurring near the scalp along with the electrical activity of nerve cells may be measured.

In the following explanation, the measuring points are numbered 1, 2, . . . , N and the result of A/D conversion of a potential $b_{i,t}$ (an analog value) acquired by an electrode 12 at an i-th point at a time t is denoted by an output value $x_{i,t}$ (a digital value). In the flowing explanation, the time t starts from 0 and is expressed by an integer value counted in the above clock unit although other expression can be used.

Assuming that an electrode situated at an i-th point is selected by the multiplexer 15 at a time t in the electroencephalograph 11, the A/D converter 16 of the electroencephalograph 11 outputs an output value $x_{i,t}$ that is an A/D-converted potential $b_{i,t}$ at the time t in the measuring mode. On the other hand, in the calibration mode, the electroencephalograph 11 outputs, at the time t, an output value $x_{i,s}$ that is an A/D-converted potential $b_{i,s}$ at a current or past sample holding time s closest to the time t.

For easier understanding, the mode of making a round of all electrodes in a given order in a cycle N/F is discussed below. In this mode, the order of electrodes can be determined so that the number i of an electrode selected by the multiplexer 15 at a time t is as follows:

$i=\text{modulo}(t,N)+1.$

Moreover, the current or past sample holding time s closest to the time t is $s=\text{floor}(t/N)\times N.$ In the above, modulo (. , .) means the remainder of division of integers and floor (.) means an integer resulting from rounding down a fraction.

Figure 3:
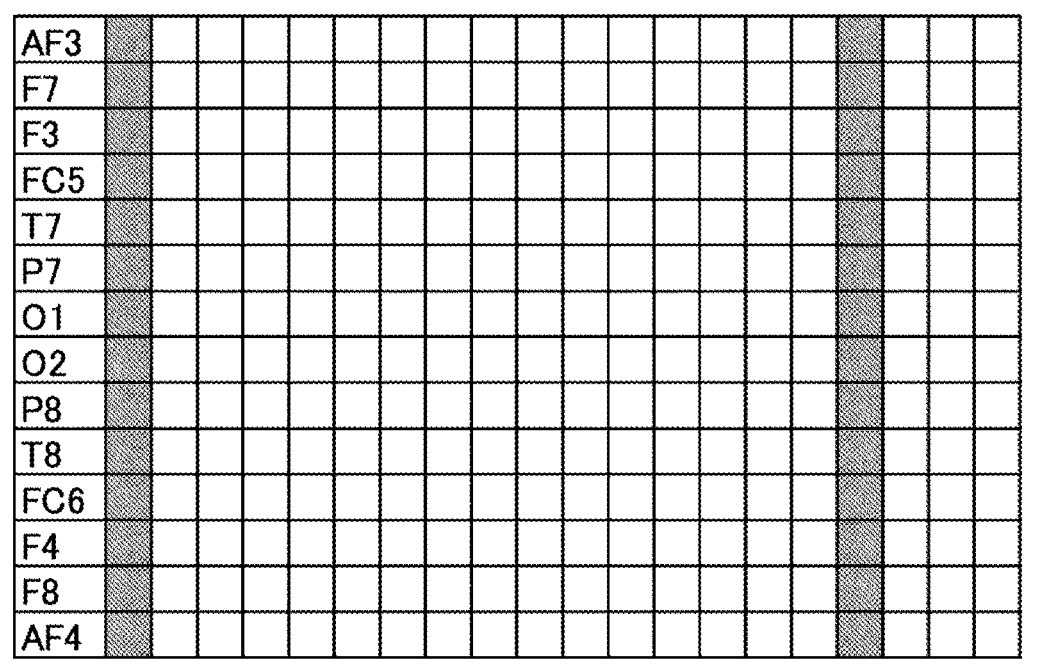
Figure 4:
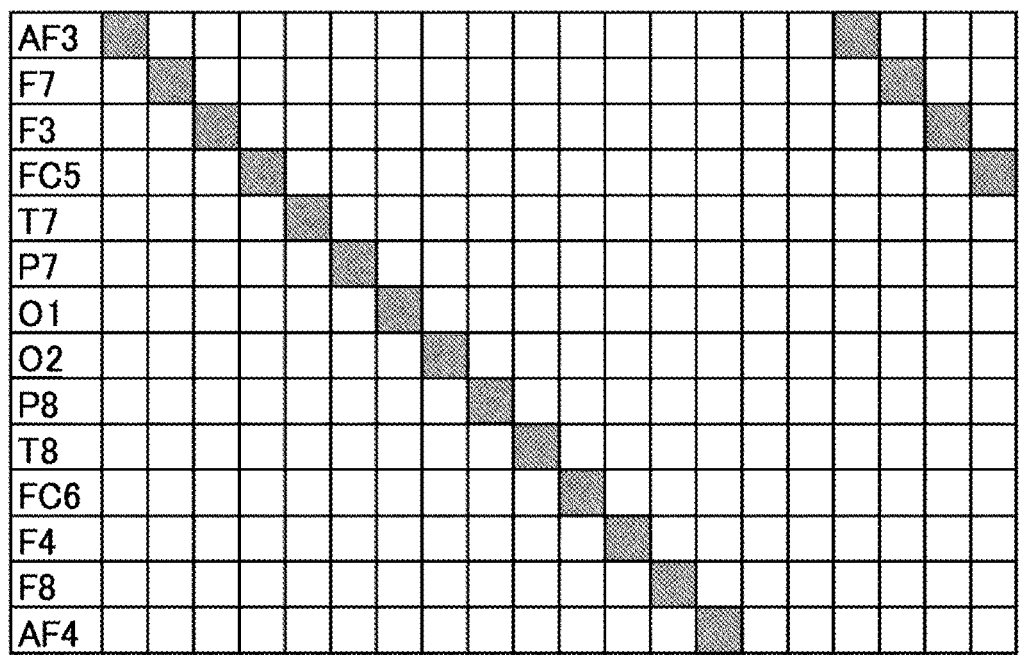
FIG. 4 is a time table presenting the points and the times of electrical activity obtained in the measuring mode.

FIG. 3 is a time table presenting the points and the times of electrical activity obtained in the calibration mode. FIG. 4 is a time table presenting the points and the times of electrical activity obtained in the measuring mode. The following explanation will be made with reference to these figures.

In the time tables shown in these figures, the horizontal direction presents elapse of time and the ordinate presents the measuring point. An element denoted by a gray square in the tables means that the potential at a measuring point of the element is A/D-converted and output with the timing of the element. In these figures, there are 14 electrodes and two dummy measuring positions are provided so that the number of clocks in a round cycle is a power of 2.

As shown in FIG. 3, in the calibration mode, the potentials at all measuring positions are simultaneously acquired and the potentials are successively A/D-converted and output in sequence, whereby the gray squares are arranged in a vertical line at an interval of round cycle.

As shown in FIG. 4, in the measuring mode, the potentials at the measuring positions are successively acquired, A/D-converted, and output, whereby the gray squares are arranged in a diagonal line of 45 degrees at intervals of round cycle.

In the following explanation, for easier understanding, a set P of which elements are pairs of i and t to process among the output values $x_{i,t}$ (in other words, a pair (i, t) is the suffixes of an output value remaining as a result of thinning out) is assumed. Furthermore, a set of times during the calibration mode is denoted by Q and a set of times during the measuring mode is denoted by R.

For example, when digital information is acquired from the above-described electroencephalograph 11 in the calibration mode from a time 0 to a time 3N−1 and in the measuring mode from a time 3N to a time 6N−1, the sets P, Q, and R at the time 6N−1 are as follows:

$$P=\{(1,0),(2,0),\ldots,(N,0),$$

$$(1,N),(2,N),\ldots,(N,N),$$

$$(1,2N),(2,2N),\ldots,(N,2N),$$

$$(1,3N),(2,3N+1),\ldots,(N,4N-1),$$

$$(1,4N),(2,4N+1),\ldots,(N,5N-1),$$

$$(1,5N),(2,5N+1),\ldots,(N,6N-1)\}$$

$$Q=\{0,1,2,\ldots,3N-1\|; \text{ and}$$

$$R=\{3N,3N+1,3N+2,\ldots,6N-1\}.$$

Here, if elements are added as appropriate each time data are acquired, the sets P, Q, and R can be processed online. Moreover, when measurement data are acquired collectively, the sets P, Q, and R can be assumed to be constants. This corresponds to offline processing.

First, in acquiring digital information in the above-described round order, for a sample holding time s, $$(1,s)\in P\&(2,s)\in P\&\ldots\&(N,s)\in P$$

is established. In other words, a set of which the elements are all sample holding times is obtained by $$\{s|(1,s)\in P\&(2,s)\in P\&\ldots\&(N,s)\in P\}.$$

Moreover, times other than the sample holding times s in the calibration mode t∈Q, $$\{(i,t)|t\in Q\&(i,t)\in P\}$$

is an empty set.

Additionally, for a time t∈R in the measuring mode, a set:

$$\{(i,t)|(i,t)\in P\}$$

has one element. Moreover, any time at which a measured value corresponding to a point i is obtained is obtained by:

$$\{t|(i,t)\in P\}.$$

A time at which a measured value corresponding to a point i in the measuring mode is obtained is obtained by:

$$\{t|t\in R\&(i,t)\in P\}$$

or $$\{t|(i,t)\in P\}-\{s|(1,s)\in P\&(2,s)\in P\&\ldots\&(N,s)\in P\}$$

in which "−" presents the difference between the sets.

Data expressed by the above set notation can be interpreted as, for example, data expressed in a list comprehension, can be expressed by a sequence, a list, or the like in a program running on a computer using known techniques, and can be calculated by known processing such as iterative processing or parallel processing of the sequence, the list, or the like, and filtering.

Here, the round order can be altered as appropriate as shown in a practical example described later. Moreover, in the case of making a round as described above, only one A/D converter 16 is used. However, it may be possible to use a smaller number of A/D converters than the measuring points as shown in a practical example described later or to provide A/D converters at all measuring points and thin out the obtained measured value as disclosed in the Non Patent Literature 1. Moreover, if a sample holding circuit is used, a value at a specific time in the past can be retained. Thus, it is possible to make one A/D converter 16 behave as if there were multiple A/D converters by making the step size of the sample holding time an integral multiple of the operation clock width of the multiplexer 15 and the A/D converter 16 and adjusting the sampling time for simultaneously sampling multiple electrodes.

(Hardware for Realizing the Reconstructing Device)

The reconstructing device according to this embodiment is typically realized by a computer executing a program. The computer is connected to the electroencephalograph 11 or a storage device storing output results thereof and transmits/receives information to/from such devices.

The program executed by the computer can be distributed/sold by a server communicably connected to the computer. Additionally, it is possible to record the program on a non-transitory information recording medium such as a compact disk read only memory (CD-ROM), a flash memory, and an electrically erasable programmable ROM (EEPROM) and distribute/sell the non-transitory information recording medium.

The program is installed on a non-transitory information recording medium such as a hard disk, a solid state drive, a flash memory, or an EEPROM possessed by the computer. Then, the information processing device in this embodiment is realized by the computer. Generally, the central processing unit (CPU) of a computer reads a program from a non-transitory information recording medium to a random access memory (RAM) and interprets and executes the codes included in the program under the control of an operating system (OS) of the computer. However, with an architecture enabling mapping of a non-transitory information recording medium in a memory space accessible by the CPU, explicit loading of a program onto the RAM may sometimes be unnecessary. Here, various kinds of information necessary in the process of executing a program can temporarily be stored in the RAM.

Instead of realizing the information processing device of this embodiment by a general-purpose computer, the information processing device of this embodiment can be configured by a dedicated electronic circuit. In this mode, the program can be used as a material for creating a wiring chart, a timing chart, or the like of an electronic circuit. In such a mode, an electronic circuit fulfilling the specification prescribed in the program is configured by a field programmable gate array (FPGA) or an application specific integrated circuit (ASIC) and the electronic circuit functions as a dedicated device fulfilling the function prescribed in the program and realizes the information processing device of this embodiment.

For easier understanding, the following explanation will be made on the premise of a mode in which the reconstructing device is realized by a computer executing a program.

(Configuration of the Reconstructing Device)

Figure 5:
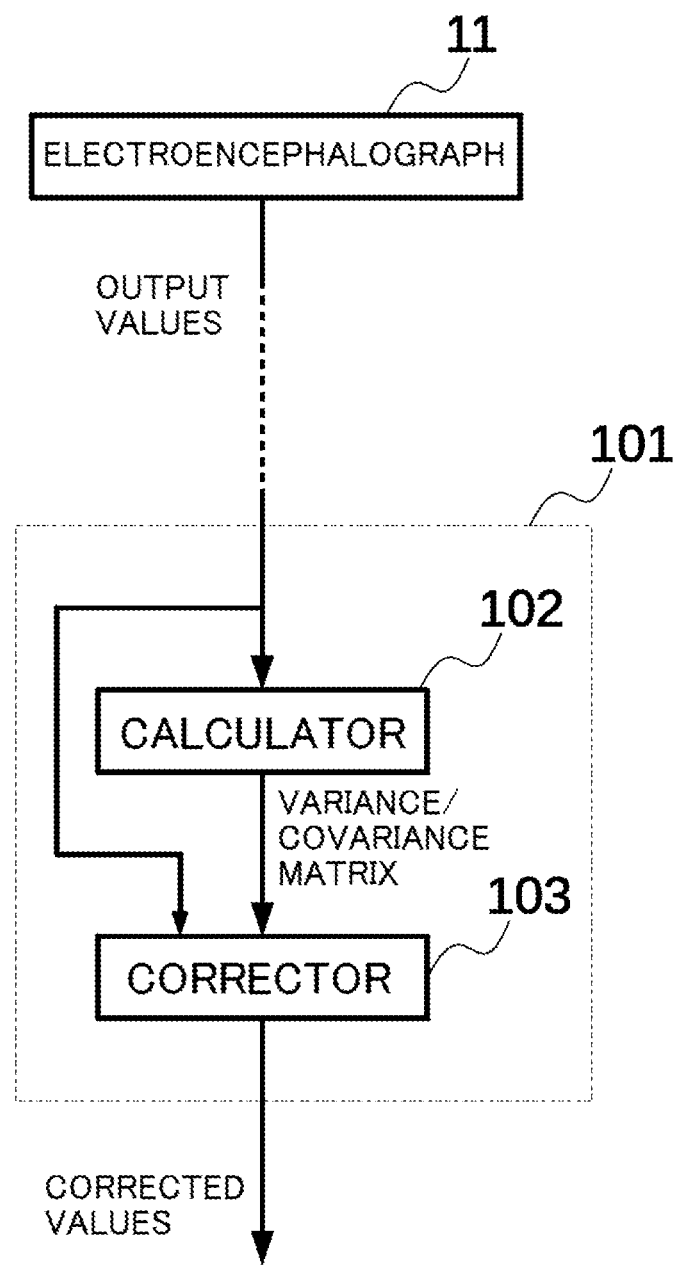
FIG. 5 is an explanatory diagram showing the configuration of the reconstructing device according to the practical example of the present disclosure.
Figure 6:
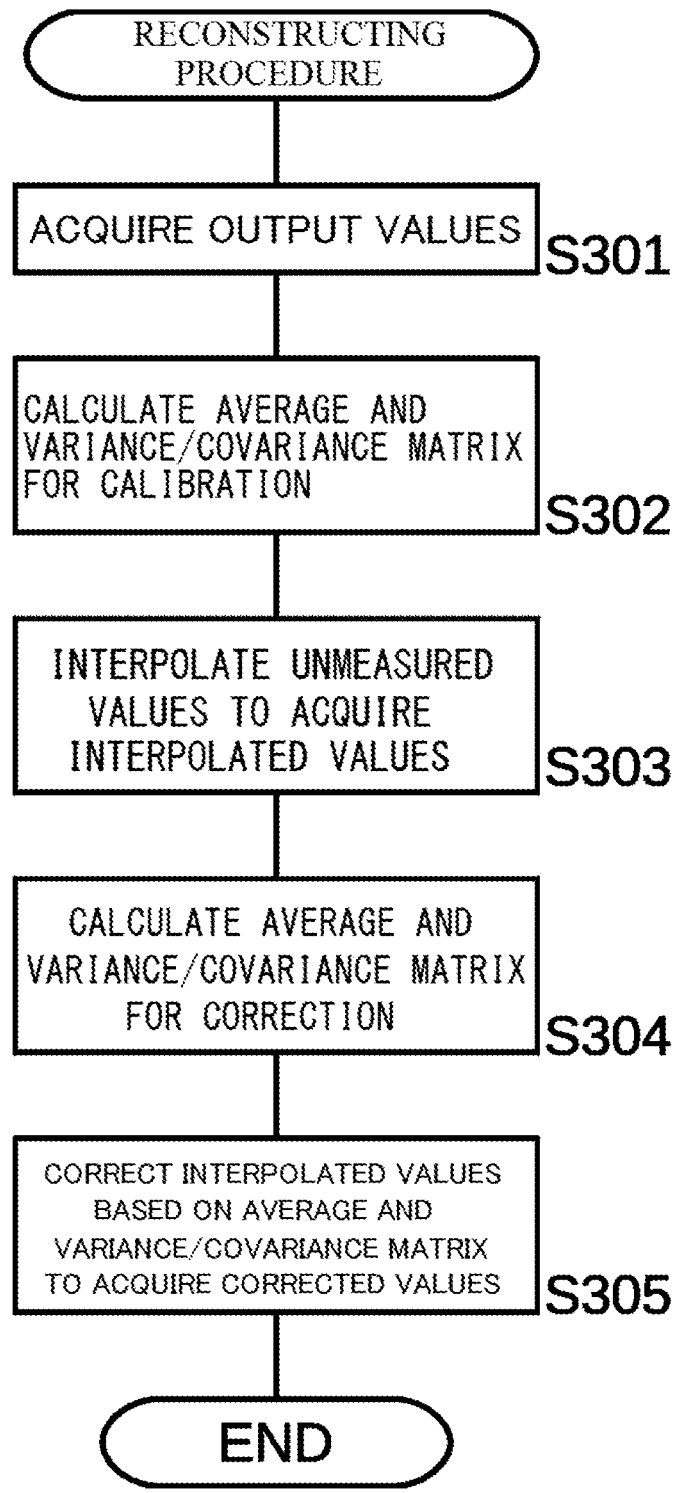
FIG. 6 is a flowchart showing the process flow of the reconstruction procedure according to the practical example of the present disclosure.

FIG. 5 is an explanatory diagram showing the configuration of the reconstructing device according to the practical example of the present disclosure. FIG. 6 is a flowchart showing the process flow of the reconstruction procedure according to the practical example of the present disclosure. As shown in this figure, a reconstructing device 101 comprises a calculator 102 and a corrector 103. Then, the reconstructing device 101 is connected directly to the electroencephalograph 11 or connected to a non-transitory recording medium or a storage device on which digital information output from the electroencephalograph 11 is stored.

First, as this reconstruction procedure starts, the reconstructing device 101 acquires output values $x_{i,t}$ of the electroencephalograph 11 (Step S301).

As described above, the output values $x_{i,t}$ are thinned out, and a set P of acquired pairs of suffixes (i, t), a set Q or R of times according to the operation mode, and the output values having suffixes that are the elements of the set P are acquired in this step.

For example, in the case of thinning out by obtaining the output values $x_{i,t}$ in making a round, $$\{(i,s)|(1,s)\in P\&(2,s)\in P\&\ldots\&(N,s)\in P, i\in\{1, 2,\ldots,N\}\}$$

is a set of all pairs of suffixes of the output values output in the calibration mode (the calibration values).

On the other hand, a set of all pairs of suffixes of the output values output in the measuring mode (the measured values) is denoted by:

$$\{(i,t)|(i,t)\in P\}-\{(j,s)|(1,s)\in P\&(2,s)\in P\&\ldots\&(N,s)\in P, j\in\{1,2,\ldots,N\}\}.$$

Next, the calculator 102 of the reconstructing device 101 calculates from the acquired output values the average value at each measuring point and a variance/covariance matrix of measuring points for calibration (Step S302). Hereafter, the average value of output values at a point i is demoted by pi, and an element in a row i and a column j of a variance/covariance matrix S, namely the variance or the covariance of output values at a point i and a point j is denoted by $S_{i,j}$.

The above values are calculated from the output values obtained in the calibration mode as follows:

$$\mu_i = \text{AVG}_{(1,s)\in P\ \&(2,s)\in P\ \&\ \ldots\ \&(N,s)\in P}[x_{i,s}]; \text{ and}$$

$$S_{i,j} = \text{AVG}_{(1,s)\in P\ \&(2,s)\in P\ \&\ \ldots\ \&(N,s)\in P}[(x_{i,s}-\mu_i)\times(x_{j,s}-\mu_j)]$$

in which $\text{AVG}_p [f (e_p)]$ is an operation for extracting an element $e_p$ satisfying a condition p specified for the suffixes and obtaining the average of the result of applying an operation f (.) to the extracted element $e_p$.

Moreover, for combining the calibration mode and the measuring mode or for performing multiple A/D conversions simultaneously, the calculation may be as follows.

$$\mu_i = \text{AVG}_{(i,t)\in P}[x_{i,t}]; \text{ and}$$

$$S_{i,j} = \text{AVG}_{(i,t)\in P\&(j,t)\in P}[(x_{i,t}-\mu_i)\times(x_{j,t}-\mu_j)].$$

Next, the corrector 103 interpolates unmeasured values that are not included in the measured values $x_{i,t}$ to obtain interpolated values $y_{i,t}$ for each of the points i (i=1, 2, . . . , N) (Step S303). As described above, the measured values $x_{i,t}$ are thinned out and if a pair (i, t) is not an element of the set P, $x_{i,t}$ is undefined. Then, such undefined elements are all interpolated.

Various techniques are applicable to the interpolation. For example, in the case of using up-sampling, first, a t-th element of a temporary variable $q_i$ for a point i is set to $x_{i,t}$ if the element is acquired and otherwise to 0 as follows:

$$q_{i,t}=x_{i,t}, \text{ if } (i,t)\in P; \text{ and}$$

$$=0, \text{ otherwise}.$$

Then, a lowpass filter of proper frequencies is applied to a time series of the temporary variable $q_i$ at a point i:

$$q_{i,0}, q_{i,1}, q_{i,2}, \ldots$$

to set:

$$y_{i,t}=x_{i,t}, \text{ if } (i,t)\in P;$$

=a t-th value of the time series as the result of applying the lowpass filter to $q_i$, whereby the interpolated values:

$$y_{i,0}, y_{i,1}, y_{i,2}, \ldots$$

are obtained.

This technique is application of a sampling frequency conversion technique. Here, the lowpass filter cycle has to be selected so as not to add high frequency components the output values $x_{i,t}$ have. Therefore, when the output values are obtained in a round order, the round cycle N may be used as the lowpass filter cycle. Alternatively, the cycle nearly double the average length after complemented with successive 0s may be used.

Additionally, various interpolation techniques such as polynomial interpolation including linear interpolation, spline interpolation, Lagrange interpolation, and Newton's interpolation may be used.

In the above example, a lowpass filter is applied without separating the calibration mode and the measuring mode. However, it may be possible to separate the two and perform interpolation only for the time t e R in the measuring mode.

Furthermore, the corrector 103 calculates an average φ and a variance/covariance matrix V for correction from the interpolated values $y_{i,t}$ in the same manner as described above (Step S304). An i-th element of the average φ and an element in a row i and a column j of the variance/covariance matrix V are calculated by:

$$\phi_i = \text{AVG}_{t\in P}[y_{i,t}]; \text{ and}$$

$$V_{i,j} = \text{AVG}_{t\in P}[(y_{i,t}-\phi_i)\times(y_{j,t}-\phi_j)].$$

When the calibration mode and the measuring mode are not separated, the calculation may be as follows:

$$\phi_i = \text{AVG}_{t\in Q\cup R}[y_{i,t}]; \text{ and}$$

$$V_{i,j} = \text{AVG}_{t\in Q\cup R}[(y_{i,t}-\mu_i)\times(y_{j,t}-\mu_j)].$$

Assuming that the measurements at the points follow a normal distribution, the variance/covariance matrices S and V should match. However, generally, the interpolation fails in sufficient reconstruction by itself and there is a shift between the variance/covariance matrices S and V.

Thus, the corrector 103 corrects $y_{i,t}$ based on the variance/covariance matrices S and V, more specifically based on their difference to obtain corrected values $z_{i,t}$ (Step S305) and ends this procedure. The corrected values $z_{i,t}$ obtained here are electrical activity reconstruction results reconstructed from the output values.

The corrected values $z_{i,t}$ are obtained as follows. First, when the output values are obtained, obviously, the following is used:

$$z_{d,t}=x_{d,t}, \text{ if } t \in R \& (d,t) \in P.$$

When $(i, t) \in P$ is not satisfied, an affine transform is applied to the remaining elements at the time t so that a variance/covariance matrix W (assumed to be) obtained from the corrected values $z_{i,t}$ matches or approximates to the variance/covariance matrix S calculated for calibration.

When the above round order is used, for a time $t \in R$ in the measuring mode, a set $\{d|(d, t) \in P\}$ has only one element. Here, this element is denoted by d as it is. Then, it is sufficient to fix an element $x_{d,t}=z_{d,t}$ and correct the other elements $(1, 2, \ldots, d-1, d+1, d+2, \text{N-th elements})$ for the time t.

Here, it is assumed that the measurements at the points at a time t follow a multidimensional normal distribution. Therefore, also when the d-th element among the measurements is fixed, the other elements should follow the multidimensional normal distribution.

Thus, in the calibration mode, a (n−1)-dimensional vector in which $\mu_1, \mu_2, \ldots, \mu_n$ are arranged excluding the d-th element is denoted by $M^{(\neq d)}$,
a (n−1)-dimensional vector in which the elements in the d-th column of the variance/covariance S excluding the d-th element are arranged is denoted by $S^{(d \neq d)}$, and
a (n−1)×(n−1) matrix as the result of eliminating the d-th row and the d-th column from the variance/covariance S is denoted by $S^{(\neq d)}$.

Then, a value $A_i$ of an i-th (n−1)-dimensional vector A presenting the average of the remaining elements after fixing the d-th element is calculated as follows:

$$A_i = M^{(\neq d)}_i + [(x_{d,t}-\mu_d)/S^{(\neq d)}_{d,d}] \times S^{(d,\neq d)}_i.$$

Moreover, the value of an element $B_{i,j}$ in a row i and a column j of a variance/covariance matrix B of the remaining elements is calculated as follows:

$$B_{i,j} = S^{(\neq d)}_{i,j} - [1/S^{(\neq d)}_{d,d}] S^{(d,\neq d)}_i \times S^{(d,\neq d)}_j.$$

Moreover, in the measuring mode, a (n−1)-dimensional vector in which $\phi_1, \phi_2, \ldots, \phi_N$ are arranged excluding the d-th element is denoted by $F^{(\neq d)}$,
a (n−1)-dimensional vector in which the elements in the d-th column of the variance/covariance V excluding the d-th element are arranged is denoted by $V^{(d,\neq d)}$, and
a (n−1)×(n−1) matrix as the result of eliminating the d-th row and the d-th column from the variance/covariance V is denoted by $V^{(\neq d)}$.

Then, a value $C_i$ of an i-th (n−1)-dimensional vector C presenting the average of the remaining elements after fixing the d-th element is calculated as follows:

$$C_i = F^{(\neq d)}_i + [(x_{d,t}-\phi_d)/V^{(\neq d)}_{d,d}] \times V^{(d,\neq d)}_i.$$

Moreover, the value of an element $D_{i,j}$ in a row i and a column j of a variance/covariance matrix D of the remaining elements is calculated as follows:

$$D_{i,j} = V^{(\neq d)}_{i,j} - [1/V^{(\neq d)}_{d,d}] V^{(d,\neq d)}_i \times V^{(d,\neq d)}_j.$$

Here, the square root ($\sqrt{X}$) of a matrix X is defined by eigenvalue decomposition:

$$X = T^{-1}LT$$

as:

$$X = T^{-1}(\sqrt{L})T$$

in which the matrix L is a diagonal matrix and the matrix $\sqrt{L}$ is a diagonal matrix of which the on-diagonal elements are the square roots of the on-diagonal elements of the matrix L.

Furthermore, a (n−1)-dimensional vector in which $y_{1,t}, y_{2,t}, \ldots, y_{N,t}$ are arranged excluding the d-th element is assumed. Then, a vector W is obtained by the following affine transform:

$$W = (\sqrt{B})(\sqrt{D})^{-1}(Y^{(\neq d)} - F^{(\neq d)}) + M^{(\neq d)}.$$

Then, as described above, in addition to setting $x_{d,t}$ as $z_{d,t}$, the vector W is set by:
(1) setting the first to (d−1)-th elements as $z_{1,t}, z_{2,t}, \ldots, z_{d-1,t}$; and
(2) setting the d-th to (N−1)-th elements as $z_{d+1,t}, \ldots, z_{N,t}$,
so as to obtain corrected values $z_{1,t}, z_{2,t}, \ldots, z_{N,t}$ that are corrected, interpolated values $y_{1,t}, y_{2,t}, \ldots, y_{N,t}$.

Repeatedly executing the above processing for each time $t \in R$, unmeasured values in the measuring mode can be interpolated and corrected. Additionally, in a mixed mode of the measuring mode and the calibration mode, the above-described processing may be repeated for all of the times $t=0, 1, 2, \ldots$.

The average and the variance/covariance matrix of the corrected values $z_{i,t}$ obtained as described above match the average and the variance/covariance matrix obtained from the output values of the measuring device 11 in the calibration mode. Therefore, more accurate reconstruction is possible than simply performing interpolation.

(Experimental Results)

Figure 7:
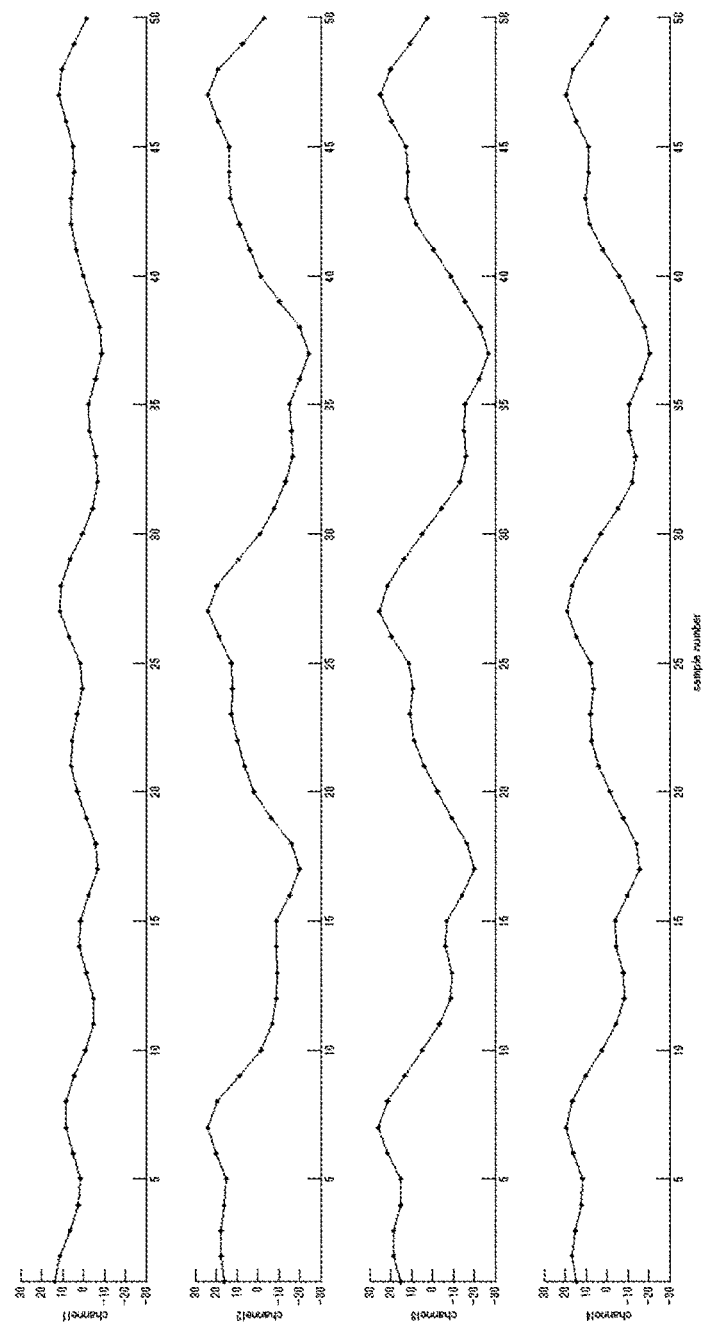
FIG. 7 is a graph presenting the original data of brain waves at all points at all times.
Figure 8:
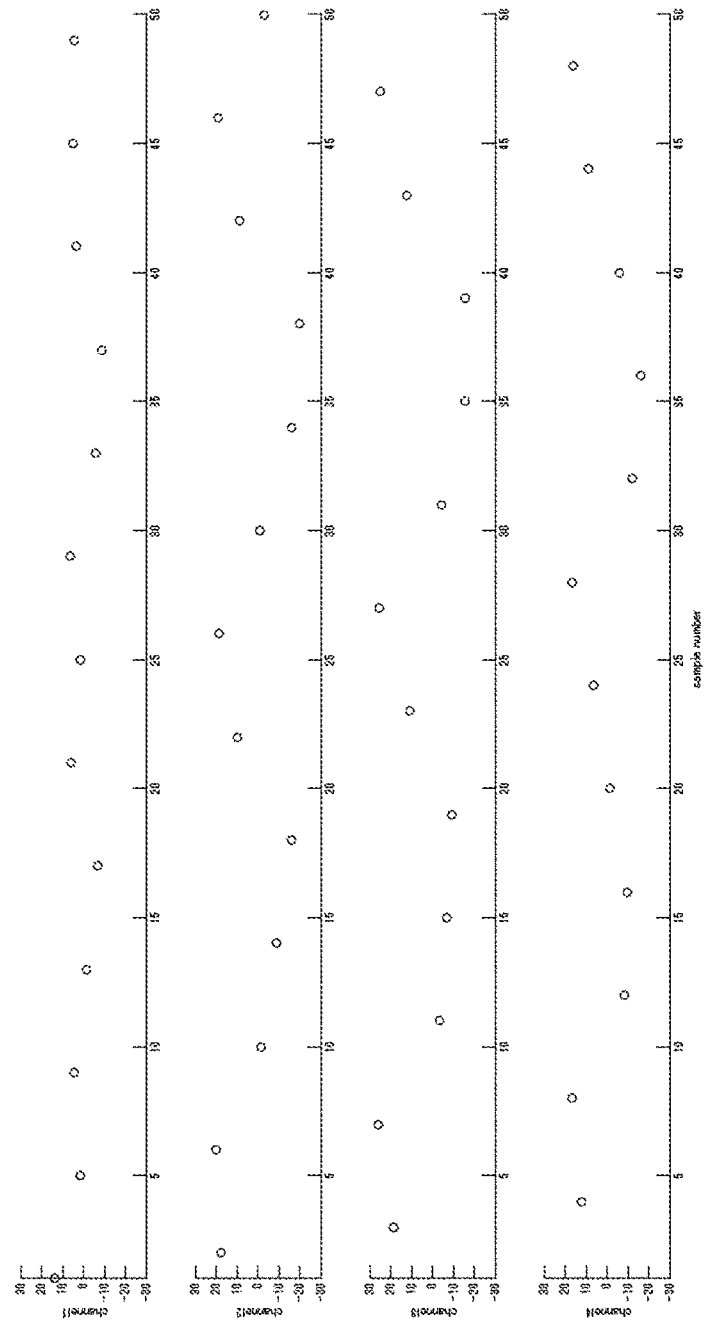
FIG. 8 is a graph presenting the measured values of brain waves after thinning out times and points.
Figure 9:
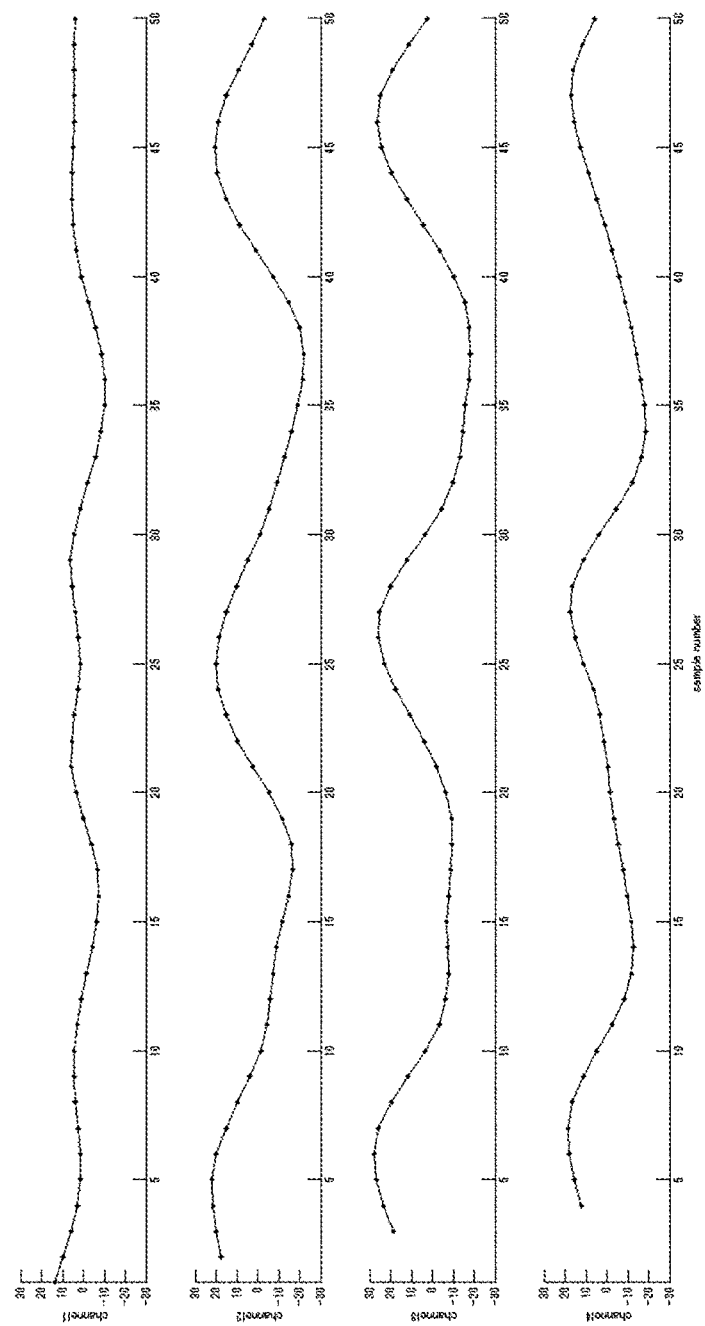
FIG. 9 is a graph presenting the interpolated values obtained by interpolating the thinned-out measured values.
Figure 10:
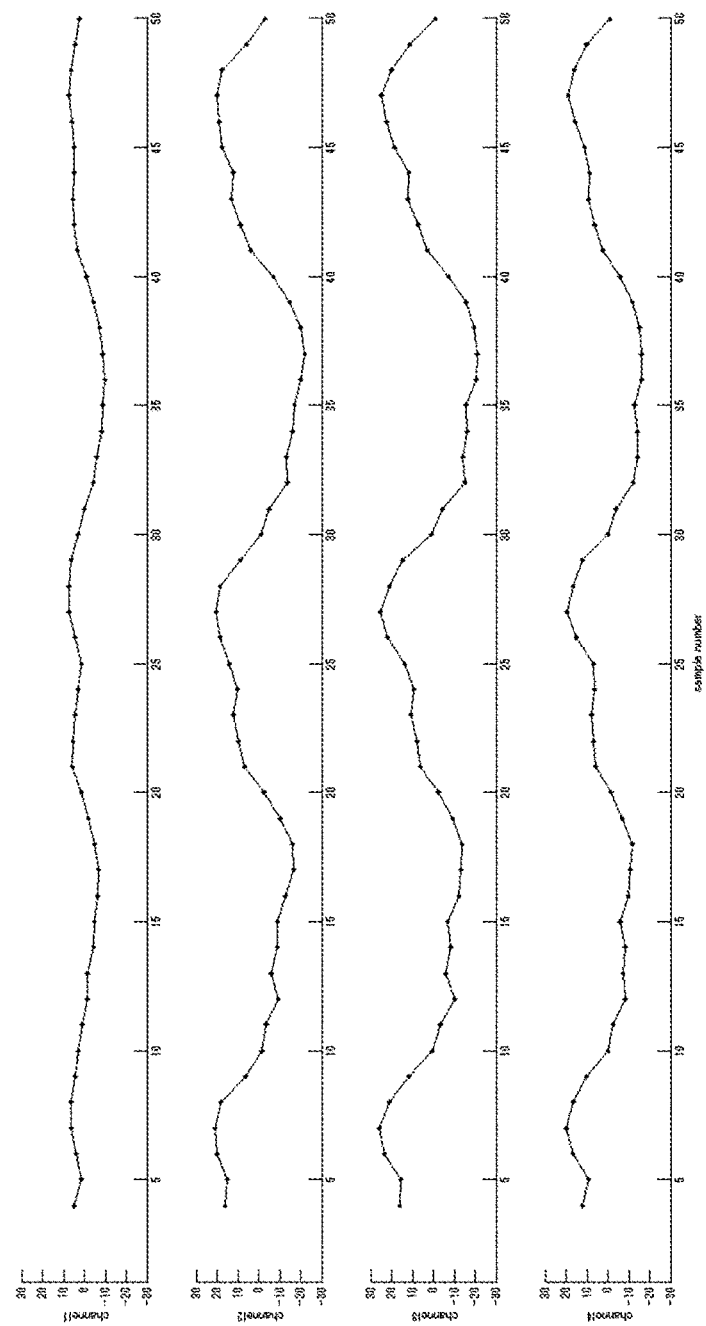
FIG. 10 is a graph presenting the corrected values obtained by correcting the interpolated values.
Figure 11:
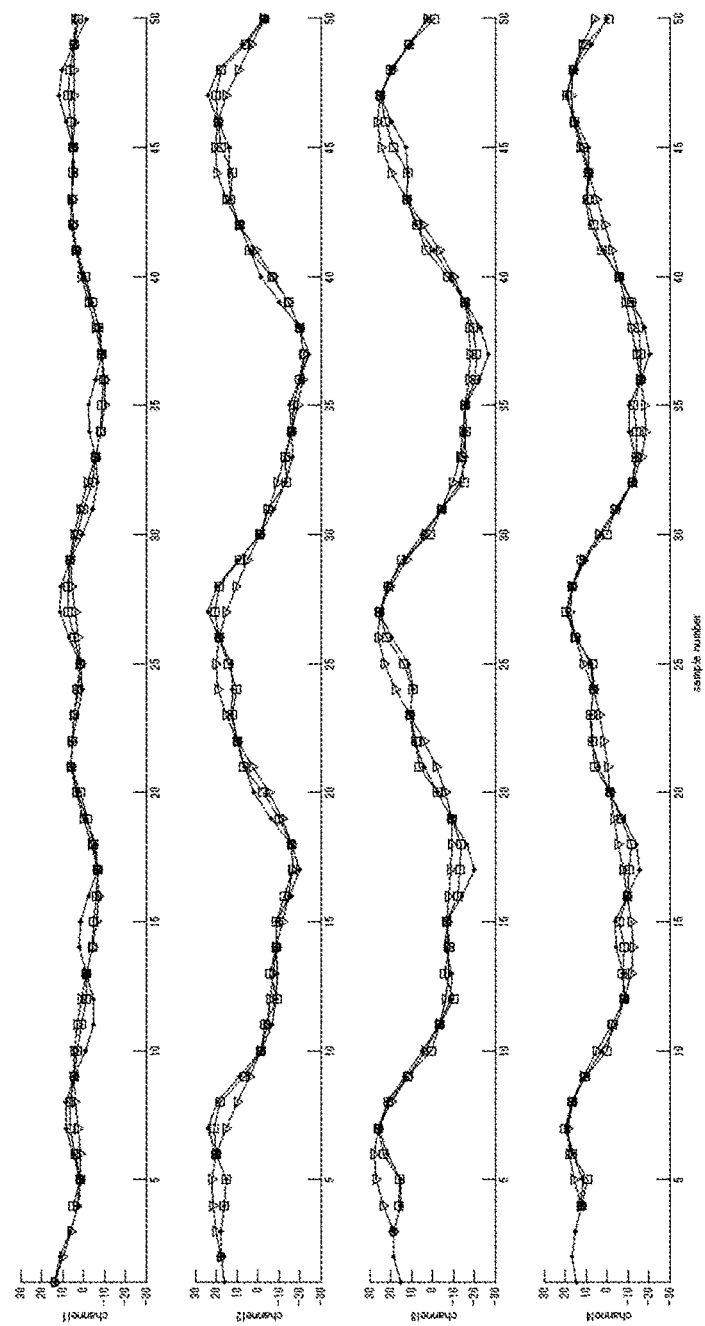
FIG. 11 is a graph of the original data, the measured values, the interpolated values, and the corrected values that are superimposed.

Results of numerical experiments are described below in which original data of scalp potentials measured at four points at all times were thinned out according to the round order in the above embodiment to obtain measured values and to what extent the original data were reconstructed from the measured values was examined. FIG. 7 is a graph presenting the original data of brain waves at all points at all times. FIG. 8 is a graph presenting the measured values of brain waves after thinning out times and points. FIG. 9 is a graph presenting the interpolated values obtained by interpolating the thinned-out measured values. FIG. 10 is a graph presenting the corrected values obtained by correcting the interpolated values. FIG. 11 is a graph of the original data, the measured values, the interpolated values, and the corrected values that are superimposed. These graphs show the events in the measuring mode. Moreover, in FIG. 11, the original data are presented by solid lines with dots (.); the measured values, by circles (○); the interpolated values, by solid lines with triangles (Δ); and the corrected values, by solid lines with squares (□).

In these figures, the interpolated values (Δ) and the original data (.) are sometimes separated. However, it is seen that even in such cases, the corrected values (□) were corrected to overlap with the original data (.) in most cases.

In the above practical example, mainly, it is assumed that only the potential of one electrode is output at a time in the measuring mode, and at a time tin the measuring mode, the potential of an electrode at a point modulo (t, N)+1 is A/D-converted and output. However, the way of selecting an electrode point can be changed in various manners.

For example, a pseudorandom number sequence obtained by randomly generating and concatenating permutations consisting of integers 1, 2, . . . , N is prepared. Then, instead of a point modulo (t, N)+1, the t-th element rand (t) in this pseudorandom number sequence is used.

For example, the number of permutations consisting of integers 1, 2, . . . , N is N!=1×2× . . . ×N. Then, in what order these permutations are concatenated may be determined by random numbers.

Additionally, instead of using all N! permutations, those resulting in the elements being each arranged as sparsely and evenly as possible may be used. For example, one or multiple Latin squares of N rows N columns are prepared, and a pseudorandom number sequence in which the elements are each sparsely and evenly arranged can be obtained by repeatedly concatenating their rows.

Additionally, as described above, the calibration mode and the measuring mode do not need to clearly be separated. In other words, it is possible to mix the calibration mode and the measuring mode by calculating the average at a point i from all measured values at the point i and calculating the variance of points i and j from all measured values simultaneously obtained at the points i and j.

In such a case, it is necessary in correcting the interpolated values to delete multiple elements from a vector presenting the average and delete multiple rows and columns from the variance/covariance matrix. In such a case, the above-described technique of deleting one element or one row and one column may be repeated for the elements or rows and columns to delete.

The mixed mode of the calibration mode and the measuring mode is also applicable to thinning out measurement results by an electroencephalograph in which one A/D converter is assigned to one electrode as used in the Non Patent Literature 1.

According to experiments by the inventors, in most cases, the matters disclosed in the Non Patent Literature 1 fail in sufficiently accurate reconstruction by themselves. According to this practical example, correction is made in consideration of the difference between the average and variance/covariance matrix obtained from the calibration values and the average and variance/covariance matrix obtained from the interpolated values so that the average and the variance/covariance matrix that should be obtained from the corrected values match the average and the variance/covariance matrix obtained from the calibration values, whereby much more accurate reconstruction is possible.

(Constrained Complement)

The Non Patent Literature 1 utilizes a low rank matrix recovery technique or a complement technique from a sparse matrix. Here, a low rank matrix recovery technique or a complement technique from a sparse matrix is also used for compressing and restoring an image.

For compressing and restoring an image, similarity in pixel value between a pixel and an adjoining or nearby pixel on the right or left, above, or below is used. The Non Patent Literature 1 assures that the brain waves can be reconstructed simply by using matrix complement. However, experiments by the inventors of this application revealed that using matrix complement widely used in the prior art fails in sufficient reconstruction of the brain waves.

On the other hand, the inventors of this application found that more accurate reconstruction is possible by expressing the relationship in similarity regarding the measuring points by the variance/covariance matrix as described above.

Thus, presumably, much more accurate reconstruction will be possible by combining the variance/covariance matrix with a low rank matrix recovery technique or a complement technique from a sparse matrix.

At this point, as the average and the variance/covariance matrix are simply used, the relationship in similarity in the positional direction is expressed but the relationship in similarity in the temporal direction is ignored.

Then, in this embodiment, the autocovariance of output values at the measuring positions and the square sum of differences between adjoining components in the temporal direction are used as the relationship in similarity in the temporal direction.

For example, for thinned-out output values, autocorrelation $R_{i,k}$ of a measuring point i and a separated time k can be calculated as follows:

$$R_{i,k} = \text{avg}_{(i,t) \in P \& (i,t+k) \in P}[(x_{i,t} - \mu_i) \times (x_{i,t+k} - \mu_i)].$$

Moreover, dissimilarity at the points 1, 2, . . . , N can be calculated by calculating the square sum of differences between adjoining components in the temporal direction for the points 1, 2, . . . , N based on the interpolated values and/or the corrected values. Furthermore, overall dissimilarity in the temporal direction of the interpolated values and/or the corrected values can be calculated by obtaining their sum.

In the above mode, correction is made so that the average vector and the variance/covariance matrix that should be calculated from the corrected values match the average vector and the variance/covariance matrix obtained from the calibration values.

Thus, in this mode, correction is made using a low rank matrix recovery technique or a complement technique from a sparse matrix constrained as follows:

(1) the average vector and the variance/covariance matrix that should be calculated from the corrected values match or approximate as close as possible to the average vector and the variance/covariance matrix obtained from the measured values, and (2a) the autocorrelation that should be calculated from the corrected values matches or approximates as close as possible to the autocorrelation obtained from the measured values, or (2b) the dissimilarity of adjoining components in the temporal direction that should be calculated from the corrected values is minimized.

In matrix complement in image processing, for suppressing the amount of calculation, matrix complement is performed under the constraint that the square sum of differences in pixel value between adjoining pixels is minimized. The combination of the above (1) and (2b) corresponds to this technique. On the other hand, the combination of the above (1) and (2a) can be used although the amount of calculation increases to some extent.

This embodiment makes much more accurate reconstruction possible by modifying a low rank matrix recovery technique or a complement technique from a sparse matrix used in image processing with the addition of constraints.

(Other Embodiments of Measuring Target and Electrical Activity)

In the above-described technique, the potential measured with the electrodes of an electroencephalograph is adopted as the electrical activity. However, the principle of the present disclosure can be generalized by measuring a target (one living body, one physical phenomenon, or the like) at multiple measuring points with various kinds of sensors and regarding as the electrical activity the current, the potential, the voltage, the power, or the like obtained from the sensors as measurement results.

In addition to the electrodes of an electroencephalograph or the like that detect the potential, output of various sensors such as a temperature sensor, an illuminance sensor, a color sensors, a pressure sensor, an odor sensor, a sound volume sensor such as a microphone, a magnetic sensor detecting magnetism, and an antenna detecting electromagnetic waves can be adopted as the electrical activity.

Here, the electrical activity measured at multiple points of a target may be of different kinds. In the example of an electroencephalograph, the potential is measured at all points with the electrodes. It may be possible to measure, on a person, the body temperature at a point, the blood pressure at a point, the color of a blood vessel at a point, and the like. The body temperature, the blood pressure, the blood vessel color, and the like of a person are mutually related and presumably, the electrical activities obtained by measuring these are also related.

Using a compatible connector that can connect various kinds of sensors in place of the electrodes 12 in the electroencephalograph 11, the configuration comprising the sample holding circuits 14, the multiplexer 15, and the A/D converter 16 can be used not only for the brain waves but also for various kinds of measurement.

Moreover, in the above-described electroencephalograph 11, the amplifiers 13 are prepared both before and after the switch S of each sample holding circuit 14. However, one or both can be omitted depending on characteristics of the electrical activity to measure.

Furthermore, videos detected by a CMOS image sensor or a CCD image sensor can be a target of the present disclosure. The Non Patent Literature 1 assures application of a technique of thinning out pixels of a still image to output of an electroencephalograph. However, as described above, the present disclosure can also reconstruct the original electrical activity from thinned-out measured values by combining and using as the constraints the relationship in positional similarity and the relationship in temporal similarity. In other words, it is possible to thin out and compress a video by simple and inexpensive hardware and reconstruct the video using the technique of the present disclosure.

In a CMOS image sensor or a CCD image sensor, in acquiring electrical activity obtained from photodiodes arranged in a matrix, it is specified in a row decoder and a column decoder for selection that a measurement in what row and what column should be output. Then, a capacitor is provided to each photodiode in a manufacturing process step to realize a configuration corresponding to the sample holding circuit 14.

In the above mode, a video image is thinned out by hardware while acquired by a CMOS image sensor. However, it is also possible to thin out a video image obtained by a conventional CMOS image sensor or the like in an ex-post manner or by software. For example, a conventional video format is used as it is for a given number of frames in the beginning of a filmed video, and some pixels are thinned out in the remaining frames to compress the video data. In such a case, the video information of the beginning part corresponds to the measured values in the calibration mode and the information of the remaining thinned-out frames corresponds to the measured values in the measuring mode.

When the filming environment and/or the scenes significantly change in a video, reconstruction may not be accurate. In such a case, it is possible to use a conventional video format for a given number of frames again and subsequently use compressed data from which some pixels have been thinned out. The same technique can be used for thinning out and compressing any measurement data in an ex-post manner.

As described above, this embodiment is not only applicable to measurement of brain waves at multiple points but also capable of thinning out/measuring and thus compressing various kinds of electrical activity data measured at multiple points of various kinds of measuring targets and reconstructing the original electrical activity from the compressed data.

SUMMARY

As described above, the reconstructing device of the present disclosure is a reconstructing device processing values output from a measuring device successively analog/digital-converting by means of a single analog/digital converter and outputting (a) electrical activity measured at multiple points of a target at the same time in a calibration mode, and (b) electrical activity measured at the multiple points at different times in a measuring mode, comprising:

a calculator calculating a variance/covariance matrix of the multiple points from calibration values output by the measuring device in the calibration mode; and a corrector obtaining corrected values from measured values output by the measuring device in the measuring mode by interpolating unmeasured values for times when the measured values are not output at each of the multiple points, wherein the corrector obtains the corrected values so that a variance/covariance matrix of the multiple points that should be calculated from the corrected values approximates to the variance/covariance matrix calculated from the calibration values.

Moreover, the reconstructing device of the present disclosure can be configured as follows:

the corrector (p) obtains interpolated values by interpolating the unmeasured values by up-sampling, polynomial interpolation, spline interpolation, Lagrange interpolation, or Newton's interpolation, and then (q) performs an affine transform on the interpolated values so that a variance/covariance matrix of the multiple points that should be calculated from the corrected values matches the variance/covariance matrix calculated from the calibration values.

Moreover, the reconstructing device of the present disclosure can be configured as follows:

the corrector obtains the corrected values by assuming that the corrected values follow a multidimensional normal distribution.

Moreover, the reconstructing device of the present disclosure can be configured as follows:

the corrector interpolates the unmeasured values by a low rank matrix recovery method.

Moreover, the reconstructing device of the present disclosure can be configured as follows:

for the electrical activity $b_{i,t}$, that should be measured at an i-th point (i=1, 2, . . . , N) among the multiple points at a time t, a value $x_{modulo\ (t,\ N)+1,\ floor\ (t/N) \times N}$ that is an analog/digital-converted $b_{modulo\ (t,\ N)+1,\ floor\ (t/N) \times N}$ is output as the calibration value at the time t in the calibration mode, and a value $x_{modulo\ (t,\ N)+1,\ t}$ that is an analog/digital-converted $b_{modulo\ (t,\ N)+1,\ t}$ is output as the measured value at the time t in the measuring mode.

Moreover, the reconstructing device of the present disclosure can be configured as follows:

for the electrical activity $b_{i,t}$ that should be measured at an i-th point (i=1, 2, ..., N) among the multiple points at a time t and a t-th element rand (t) of a pseudorandom number sequence defined by selecting in a duplicable manner and concatenating permutations of integers 1, 2, ..., N, a value $x_{rand\ (t),\ floor\ (t/N) \times N}$ that is an analog/digital-converted $b_{rand\ (t),\ floor\ (t/N) \times N}$ is output as the calibration value at the time t in the calibration mode, and a value $x_{rand\ (t),\ t}$ that is an analog/digital-converted $b_{rand\ (t),\ t}$ is output as the measured value at the time t in the measuring mode.

Moreover, the reconstructing device of the present disclosure can be configured as follows:

the pseudorandom number sequence is defined by repeatedly concatenating rows included in one or multiple N×N Latin squares.

Moreover, the reconstructing device of the present disclosure can be configured as follows:

sensors disposed at the multiple points are connected to a selection circuit selecting input to the analog/digital converter (a) via a sample holding circuit in the calibration mode, and (b) without the sample holding circuit in the measuring mode.

The reconstructing method of the present disclosure is a reconstructing method for a reconstructing device processing values output from a measuring device successively analog/digital-converting by means of a single analog/digital converter and outputting (a) electrical activity measured at multiple points of a target at the same time in a calibration mode, and (b) electrical activity measured at the multiple points at different times in a measuring mode to calculate a variance/covariance matrix of the multiple points from calibration values output by the measuring device in the calibration mode, and obtains corrected values from measured values output by the measuring device in the measuring mode by interpolating unmeasured values for times when the measured values are not output at each of the multiple points, wherein the corrected values are obtained so that a variance/covariance matrix of the multiple points that should be calculated from the corrected values approximates to the variance/covariance matrix calculated from the calibration values.

The reconstructing device of the present disclosure is a reconstruction device processing measured values obtained from multiple points of a target by thinning out and measuring or measuring and then thinning out, comprising:

a calculator calculating a variance/covariance matrix of the multiple points from calibration values measured at different points at the same time among the measured values; and a corrector obtaining corrected values by interpolating unmeasured values for times when the measured values are absent at each of the multiple points, wherein the corrector obtains the corrected values so that a variance/covariance matrix of the multiple points that should be calculated from the corrected values approximates to the variance/covariance matrix calculated from the calibration values.

The reconstructing method of the present disclosure is a reconstructing method for a reconstruction device processing measured values obtained from multiple points of a target by thinning out and measuring or measuring and then thinning out to calculate a variance/covariance matrix of the multiple points from calibration values measured at different points at the same time among the measured values, and obtain corrected values by interpolating unmeasured values for times when the measured values are absent at each of the multiple points, wherein the corrected values are obtained so that a variance/covariance matrix of the multiple points that should be calculated from the corrected values approximates to the variance/covariance matrix calculated from the calibration values.

The program according to the present disclosure causes a computer to function as parts included in the above reconstructing device.

The non-transitory computer-readable information recording medium according to the present disclosure has the above program stored.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the priority based on Japanese Patent Application No. 2015-112113, filed in Japan on Tuesday, Jun. 2, 2015, and the content of this basic application is incorporated herein to the fullest legal extent in the designated nation.

INDUSTRIAL APPLICABILITY

The present disclosure can provide a reconstructing device reconstructing activity at multiple points at times from measured values obtained from multiple points of a target by thinning out and measuring or measuring and then thinning out, a reconstructing method, a program for realizing them by a computer, and a non-transitory computer-readable information recording medium storing the program.

REFERENCE SIGNS LIST

11 Electroencephalograph
12 Electrode
13 Amplifier
14 Sample holding circuit
15 Multiplexer
16 A/D converter
101 Reconstructing device
102 Calculator
103 Corrector

The invention claimed is:

1. A reconstruction device comprising:
sensors configured to be disposed at multiple points of a target respectively;
a non-transitory memory for storing a program; and
a processor for executing the program, the program comprising:
an obtaining code that causes the processor to obtain, from the sensors, values at the multiple points of the target by thinning out and measuring or measuring and then thinning out the values,
a calculating code that causes the processor to calculate a variance-covariance matrix of the multiple points from calibration values measured at different points on the target at the same time among the values; and
a correcting code that causes the processor to obtain corrected values by interpolating unmeasured values for times when the values are absent at one or more of the multiple points, so that a variance-covariance matrix of the multiple points calculated from the corrected values approximates the variance-covariance matrix calculated from the calibration values.

2. The reconstructing device according to claim 1, further comprising:
a single analog/digital converter successively analog/digital-converting and outputting:
(a) electrical activity measured at the multiple points at the same time in a calibration mode, and
(b) electrical activity measured at the multiple points at different times in a measuring mode,
and wherein:
the calculating code causes the processor to calculate the variance-covariance matrix of the multiple points from calibration values output by the measuring device in the calibration mode, and
the correcting code causes the processor to interpolate unmeasured values for times when the measured values are not output at each of the multiple points from measured values output by the measuring device in the measuring mode.

3. The reconstructing device according to claim 2, wherein
for the electrical activity $b_{i,t}$ that should be measured at an i-th point (i=1, 2, ..., N) among the multiple points at a time t,
a value $x_{modulo(t,N)+1, floor(t/N) \times N}$ that is an analog/digital-converted $b_{modulo(t,N)+1, floor(t/N) \times N}$ is output as the calibration value at the time t in the calibration mode, and
a value $x_{modulo(t,N)+1,t}$ that is an analog/digital-converted $b_{modulo(t,N)+1,t}$ is output as the measured value at the time tin the measuring mode.

4. The reconstructing device according to claim 2, wherein
for the electrical activity $b_{i,t}$ that should be measured at an i-th point (i=1, 2, ..., N) among the multiple points at a time t and a t-th element rand(t) of a pseudorandom number sequence defined by selecting in a duplicable manner and concatenating permutations of integers 1, 2, ..., N,
a value $x_{rand(t), floor(t/N) \times N}$ that is an analog/digital-converted $b_{rand(t), floor(t/N) \times N}$ is output as the calibration value at the time t in the calibration mode, and
a value $x_{rand(t),t}$ that is an analog/digital-converted $b_{rand(t),t}$ is output as the measured value at the time t in the measuring mode.

5. The reconstructing device according to claim 4, wherein
the pseudorandom number sequence is defined by repeatedly concatenating rows included in one or multiple N×N Latin squares.

6. The reconstructing device according to claim 2, further comprising a selection circuit connected to the sensors and a sample holding circuit, the selection circuit selecting input to the single analog/digital converter
(a) via the sample holding circuit in the calibration mode, and
(b) without the sample holding circuit in the measuring mode.

7. The reconstructing device according to claim 1, wherein
the correcting code causes the processor to:
obtain interpolated values by interpolating the unmeasured values by up-sampling, polynomial interpolation, spline interpolation, Lagrange interpolation, or Newton's interpolation, and then
perform an affine transform on the interpolated values so that a variance-covariance matrix of the multiple points that should be calculated from the corrected values matches the variance-covariance matrix calculated from the calibration values.

8. The reconstructing device according to claim 7, wherein
the correcting code causes the processor to obtain the corrected values by assuming that the corrected values follow a multidimensional normal distribution.

9. The reconstructing device according to claim 1, wherein
the correcting code causes the processor to interpolate the unmeasured values by a low rank matrix recovery method.

10. The reconstruction device according to claim 1, configured as an electroencephalograph wherein the sensors are scalp electrodes, each scalp electrode configured for making contact with a point on a scalp of a subject, to measure scalp potential.

11. A reconstructing method for use in a reconstruction device comprising sensors disposed at multiple points of a target respectively comprising:
obtaining, from the sensors, values at the multiple points by thinning out and measuring or measuring and then thinning out; and to then:
calculating a variance-covariance matrix of the multiple points from calibration values measured at different points at the same time among the measured values, and
obtaining corrected values by interpolating unmeasured values for times when the measured values are absent at one or more of the multiple points, so that a variance-covariance matrix of the multiple points calculated from the corrected values approximates the variance-covariance matrix calculated from the calibration values.

12. A non-transitory computer-readable information recording medium storing a computer program for use by a computer processor comprising:
an obtaining code that causes the processor to obtain values, from sensors disposed at multiple points of a target, by thinning out and measuring or measuring and then thinning out the values
a calculating code that causes the processor to calculate a variance-covariance matrix of the multiple points from calibration values measured at different points on the target at the same time among the values; and
a correcting code that causes the processor to obtain corrected values by interpolating unmeasured values for times when values are absent at one or more of the multiple points, so that a variance-covariance matrix of the multiple points calculated from the corrected values approximates the variance-covariance matrix calculated from the calibration values.

13. A non-transitory computer-readable information recording medium storing computer code for causing a processor to perform the method according to claim 11.

* * * * *